United States Patent
Lang et al.

(10) Patent No.: US 6,503,283 B1
(45) Date of Patent: Jan. 7, 2003

(54) DYEING COMPOSITION FOR KERATIN FIBERS AND DYEING METHOD USING SAME

(75) Inventors: Gérard Lang, Regaar (FR); Marie-Pascale Audousset, Asniéres (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/331,251

(22) PCT Filed: Oct. 7, 1998

(86) PCT No.: PCT/FR98/02144

§ 371 (c)(1),
(2), (4) Date: Aug. 16, 1999

(87) PCT Pub. No.: WO99/20234

PCT Pub. Date: Apr. 29, 1999

(30) Foreign Application Priority Data

Oct. 22, 1997 (FR) .............................. 97 13242

(51) Int. Cl.$^7$ ................................. A61K 7/13
(52) U.S. Cl. .................. 8/407; 8/410; 8/411; 8/412; 8/416; 8/421; 8/423; 8/426; 8/409
(58) Field of Search ..................... 8/405, 407, 408, 8/409, 410, 411, 412, 416, 421, 423, 426

(56) References Cited

U.S. PATENT DOCUMENTS

| | | | | |
|---|---|---|---|---|
| 3,985,499 A | | 10/1976 | Lang et al. ............. | 8/426 |
| 4,025,301 A | | 5/1977 | Lang et al. ............. | 8/405 |
| 4,297,098 A | * | 10/1981 | Dasher et al. .......... | 8/412 |
| 4,391,603 A | * | 7/1983 | Rosenbaum et al. ..... | 8/424 |
| 4,425,132 A | * | 1/1984 | Grollier et al. ......... | 8/405 |
| 4,961,925 A | * | 10/1990 | Tsujino et al. .......... | 8/406 |
| 4,985,955 A | * | 1/1991 | Grollier et al. ......... | 8/406 |
| 5,041,143 A | * | 8/1991 | Lang et al. ............. | 8/415 |
| 5,350,424 A | * | 9/1994 | Shansky ................. | 8/406 |
| 5,919,273 A | * | 7/1999 | Rondeau et al. ........ | 8/426 |
| 6,001,135 A | * | 12/1999 | Rondeau et al. ........ | 8/426 |
| 6,004,355 A | * | 12/1999 | Dias et al. .............. | 8/406 |
| 6,022,381 A | * | 2/2000 | Dias et al. .............. | 8/406 |

FOREIGN PATENT DOCUMENTS

| EP | 0 714 954 | 6/1996 |
|---|---|---|
| WO | WO 95/01772 | 1/1995 |
| WO | WO 95/15144 | 6/1995 |

OTHER PUBLICATIONS

Venkataraman, The Chemistry of Synthetic Dyes, vol. V, Academic Press, 1971 (No Month Available).*
English language Derwent Abstract for EP 0 714 954, Jun. 1996.

* cited by examiner

Primary Examiner—Margaret Einsmann
(74) Attorney, Agent, or Firm—Finnegan, Henderson, Farabow, Garrett & Dunner, L.L.P.

(57) ABSTRACT

The invention relates to a ready-to-use composition for dyeing keratin fibers, and in particular human keratin fibers such as the hair, comprising, in a medium which is suitable for dyeing, at least one cationic direct dye and at least one auto-oxidizable dye, as well as to the dyeing process using this composition.

43 Claims, No Drawings

DYEING COMPOSITION FOR KERATIN FIBERS AND DYEING METHOD USING SAME

The invention relates to a composition for dyeing keratin fibres, and in particular human keratin fibres such as the hair, comprising, in a medium which is suitable for dyeing, at least one cationic direct dye and at least one auto-oxidizable dye, as well as to the dyeing process using this composition.

It is known practice to dye keratin fibres, and in particular human hair, with dye compositions containing auto-oxidizable dyes such as benzene derivatives containing at least three hydroxyl and/or amino groups and indole derivatives, such as 5,6-dihydroxyindole. These auto-oxidizable dyes have the particular feature of being able to be oxidized without any oxidizing agent other than atmospheric oxygen, to give rise to coloured and colouring molecules. However, the colorations obtained using these dyes are still not satisfactory, in particular as regards their intensity and their chromaticity.

It is also known practice to dye keratin fibres with direct dyes, and in particular with cationic direct dyes. Direct dyes have the drawback, when they are incorporated into dye compositions, of leading to colorations which are of insufficient staying power, in particular with respect to shampooing.

The Applicant has now discovered that it is possible to obtain novel compositions for dyeing keratin fibres, which are capable of leading to intense, unselective colorations which show good resistance to the various attacking factors to which the hair may be subjected, by combining at least one cationic direct dye and at least one auto-oxidizable dye.

This discovery forms the basis of the present invention.

A first subject of the invention is thus a ready-to-use composition for dyeing keratin fibres, and in particular human keratin fibres such as the hair, characterized in that it comprises, in a medium which is suitable for dyeing:
- at least one cationic direct dye,
- at least one auto-oxidizable dye.

The ready-to-use dye composition in accordance with the invention leads to intense, chromatic colorations which show low selectivity and excellent properties of resistance both with respect to atmospheric agents such as light and bad weather, and with respect to perspiration and the various treatments to which the hair may be subjected (washing, permanent-waving).

A subject of the invention is also a process for dyeing keratin fibres using this ready-to-use dye composition.

The cationic direct dye(s) which can be used in the ready-to-use dye composition in accordance with the invention is (are) preferably chosen from cationic aminoanthraquinone dyes, cationic monoazo or diazo dyes and cationic naphthoquinone dyes.

By way of example, mention may be made in particular of [8-[(p-aminophenyl)azo]-7-hydroxy-2-naphthyl] trimethylammonium chloride (also known as Basic Brown 16 or Arianor Mahogany 306002 in the Color Index), 3-[(4-amino-6-bromo-5,8-dihydro-1-hydroxy-8-imino-5-oxo-2-naphthalenyl)amino]-N,N,N-trimethylbenzenaminium chloride (also known as Basic Blue 99 or Arianor Steel Blue 306004 in the Color Index), 7-hydroxy-8-[(2-methoxyphenyl)azo]-N,N,N-trimethyl-2-naphthalenaminium chloride (also known as Basic Red 76 or Arianor Madder Red in the Color Index), [8-[(4-amino-2-nitrophenyl)azo]-7-hydroxy-2-naphthyl]-trimethylammonium chloride (also known as Basic Brown 17 or Arianor Sienna Brown 306001 in the Color Index) and 3-[(4,5-dihydro-3-methyl-5-oxo-1-phenyl-1H-pyrazol-4-yl) azo]-N,N,N-trimethylbenzenaminium chloride (also known as Basic Yellow 57 or Arianor Straw Yellow 306005 in the Color Index).

The cationic direct dye(s) can also be chosen from:
a) the compounds of formula (I) below:

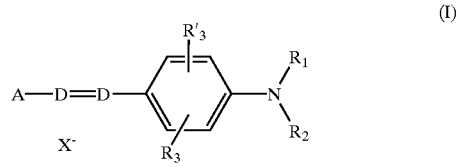

in which:
D represents a nitrogen atom or a —CH group,
$R_1$ and $R_2$, which may be identical or different, represent a hydrogen atom; a $C_1$–$C_4$ alkyl radical which can be substituted with a —CN, —OH or —NH$_2$ radical; or form, with a carbon atom of the benzene ring, an optionally oxygenated or nitrogenous heterocycle, which can be substituted with one or more $C_1$–$C_4$ alkyl radicals; a 4'-aminophenyl radical,
$R_3$ and $R'_3$, which may be identical or different, represent a hydrogen or halogen atom chosen from chlorine, bromine, iodine and fluorine, or a cyano, $C_1$–$C_4$ alkoxy or acetyloxy radical,
$X^-$ represents an anion preferably chosen from chloride, methyl sulphate and acetate,
A represents a group chosen by structures A1 to A19 below:

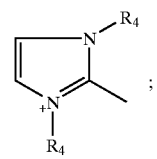

A1

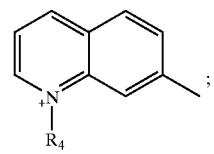

A2

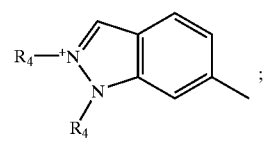

A3

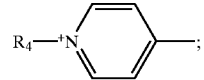

A4

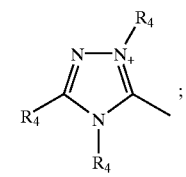

A5

-continued

A₆
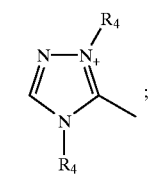

A₇
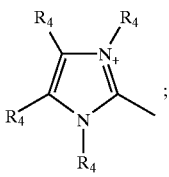

A₈
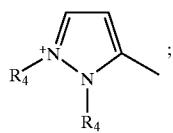

A₉
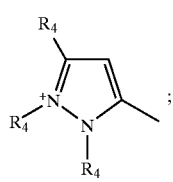

A₁₀
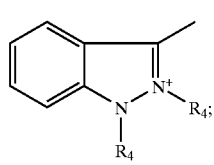

A₁₁
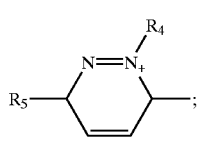

A₁₂
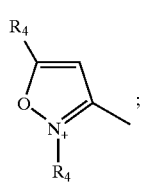

A₁₃
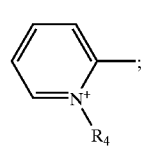

A₁₄
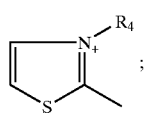

-continued

A₁₅
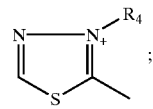

A₁₆
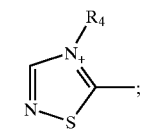

A₁₇
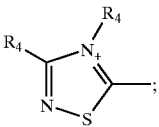

A₁₈
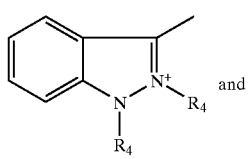
and

A₁₉
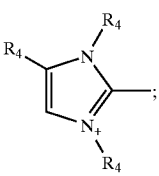

in which $R_4$ represents a $C_1$–$C_4$ alkyl radical which can be substituted with a hydroxyl radical and $R_5$ represents a $C_1$–$C_4$ alkoxy radical, with the proviso that when D represents —CH, when A represents $A_4$ or $A_{13}$ and when $R_3$ is other than an alkoxy radical, then $R_1$ and $R_2$ do not simultaneously denote a hydrogen atom;

b) the compounds of formula (II) below:

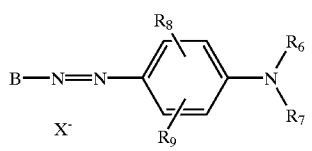

(II)

in which:
$R_6$ represents a hydrogen atom or a $C_1$–$C_4$ alkyl radical,
$R_7$ represents a hydrogen atom, an alkyl radical which can be substituted with a —CN radical or with an amino group, a 4'-aminophenyl radical or forms, with $R_6$, an optionally oxygenated and/or nitrogenous heterocycle which can be substituted with a $C_1$–$C_4$ alkyl radical,
$R_8$ and $R_9$, which may be identical or different, represent a hydrogen atom, a halogen atom such as bromine, chlorine, iodine or fluorine, a $C_1$–$C_4$ alkyl or $C_1$–$C_4$ alkoxy radical or a —CN radical,
$X^-$ represents an anion preferably chosen from chloride, methyl sulphate and acetate,
B represents a group chosen by structures B1 to B6 below:

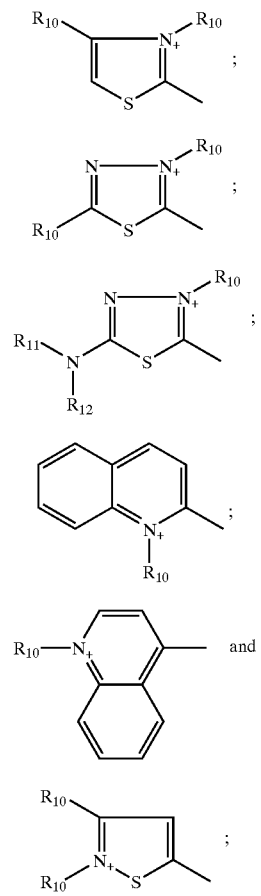

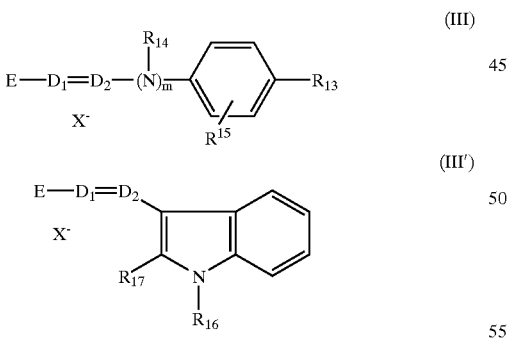

in which $R_{10}$ represents a $C_1$–$C_4$ alkyl radical, $R_{11}$, and $R_{12}$, which may be identical or different, represent a hydrogen atom or a $C_1$–$C_4$ alkyl radical;

c) the compounds of formulae (III) and (III') below:

in which:
- $R_{13}$ represents a hydrogen atom, a $C_1$–$C_4$ alkoxy radical, a halogen atom such as bromine, chlorine, iodine or fluorine, or an amino radical,
- $R_{14}$ represents a hydrogen atom, a $C_1$–$C_4$ alkyl radical or forms, with a carbon atom of the benzene ring, a heterocycle which is optionally oxygenated and/or substituted with one or more $C_1$–$C_4$ alkyl groups,
- $R_{15}$ represents a hydrogen atom or a halogen atom such as bromine, chlorine, iodine or fluorine,
- $R_{16}$ and $R_{17}$, which may be identical or different, represent a hydrogen atom or a $C_1$–$C_4$ alkyl radical, $D_1$ and $D_2$, which may be identical or different, represent a nitrogen atom or a —CH group, m=0 or 1, it being understood that when $R_{13}$ represents an unsubstituted amino group, then $D_1$ and $D_2$ simultaneously represent a —CH group and m=0, $X^-$ represents an anion preferably chosen from chloride, methyl sulphate and acetate, E represents a group chosen by structures E1 to E8 below:

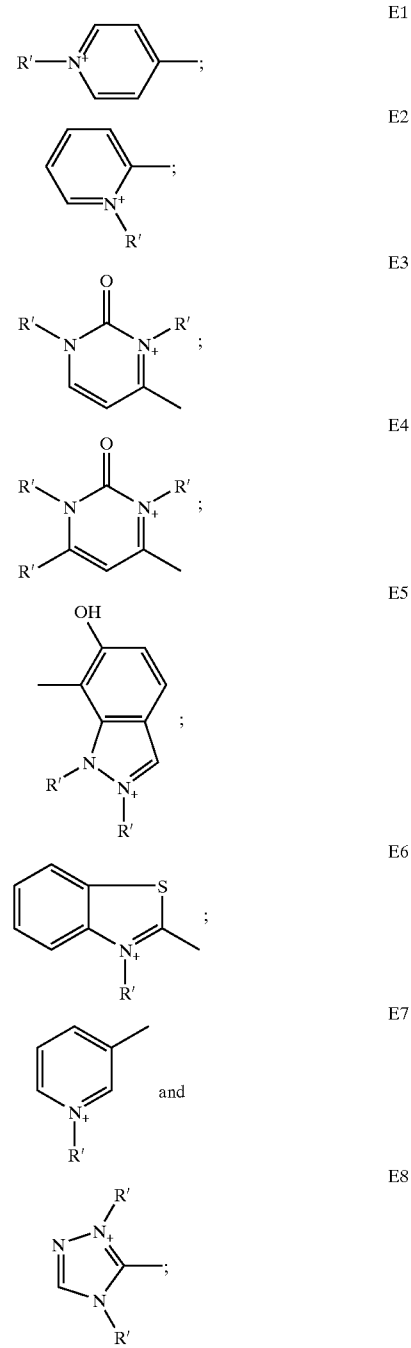

in which R' represents a $C_1$–$C_4$ alkyl radical;

when m=0 and when $D_1$ represents a nitrogen atom, then E can also denote a group of structure E9 below:

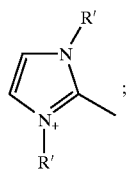

E9 in which R' represents a $C_1$–$C_4$ alkyl radical.

The cationic direct dyes of formulae (I), (II), (III) and (III') which can be used in the ready-to-use dye compositions in accordance with the invention are known compounds and are described, for example, in patent applications WO 95/01772, WO 95/15144 and EP-A-0,714,954.

Among the cationic direct dyes of formula (I) which can be used in the ready-to-use dye compositions in accordance with the invention, mention may be made more particularly of the compounds corresponding to structures (I1) to (I52) below:

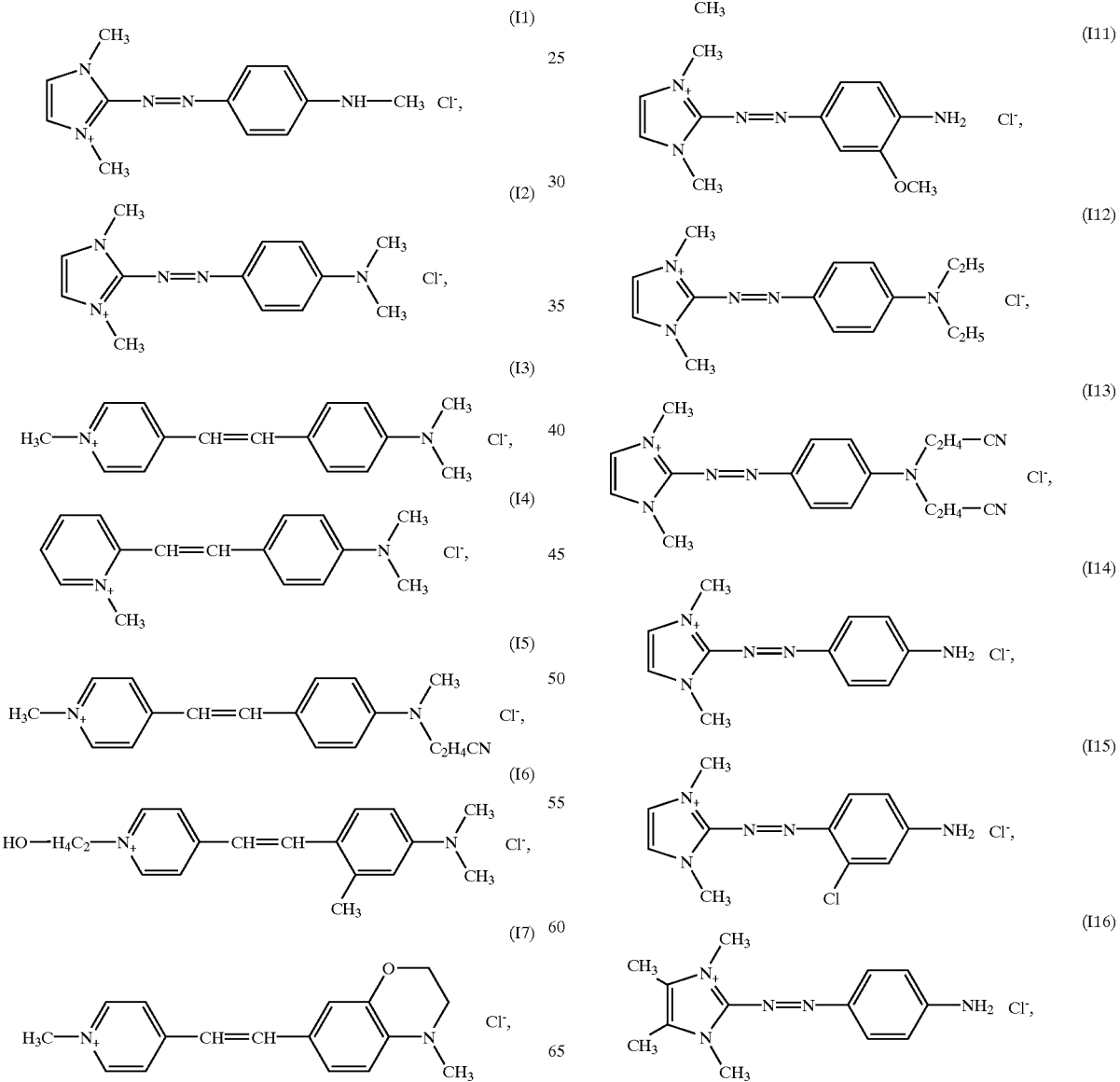

-continued (I17) (I18) (I19) (I20) (I21) (I22) (I23) (I24) (I25) (I26) (I27) (I28) (I29) (I30) (I31) (I32) (I33) (I34)

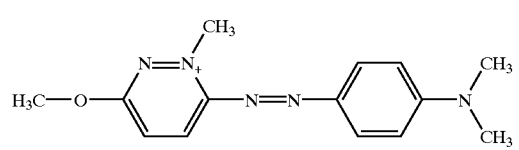
(I35) Cl⁻,
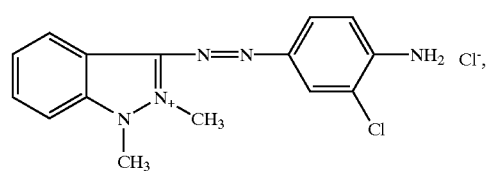
(I36) Cl⁻,
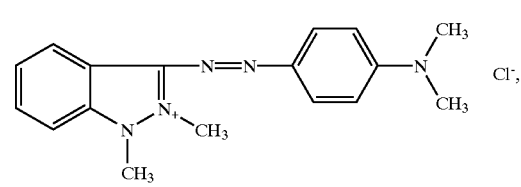
(I37) Cl⁻,
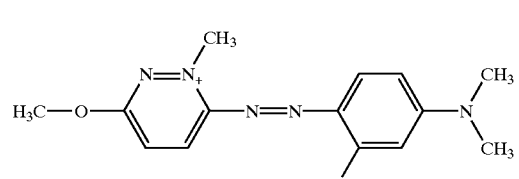
(I38) Cl⁻,
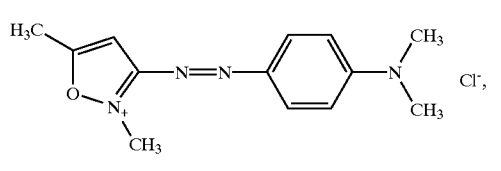
(I39) Cl⁻,
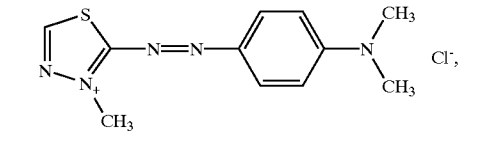
(I40) Cl⁻,
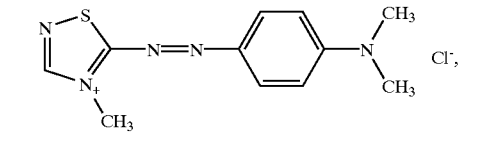
(I41) Cl⁻,
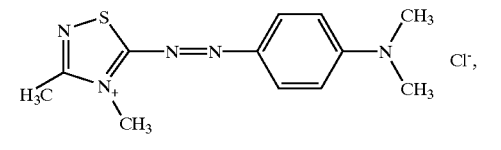
(I42) Cl⁻,
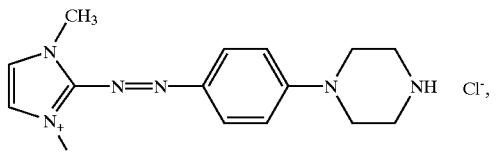
(I43) Cl⁻,
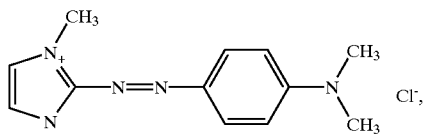
(I44) Cl⁻,
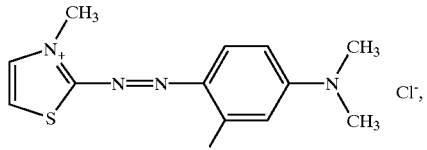
(I45) Cl⁻,
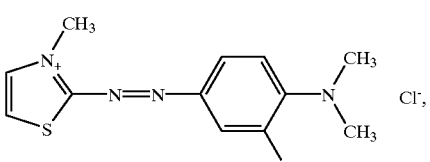
(I46) Cl⁻,
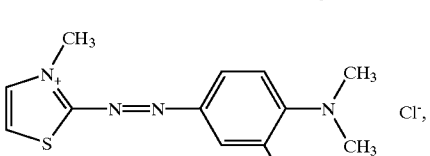
(I47) Cl⁻,
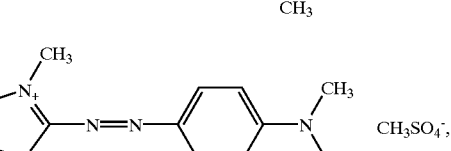
(I48) CH₃SO₄⁻,
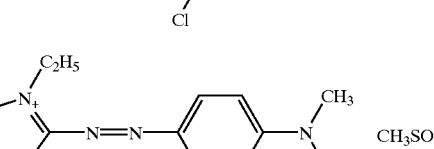
(I49) CH₃SO₄⁻,
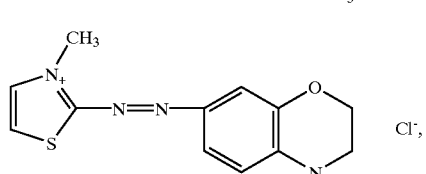
(I50) Cl⁻,
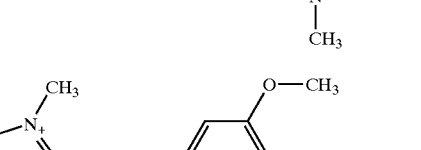
(I51) Cl⁻, and
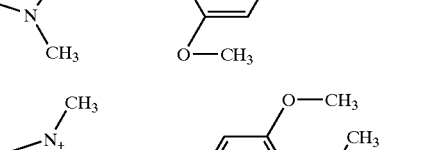
(I52) Cl⁻.

Among the compounds of structures (I1) to (I52) described above, the compounds most particularly preferred are the ones corresponding to structures (I1), (I2), (I14) and (I31).

Among the cationic direct dyes of formula (II) which can be used in the ready-to-use dye compositions in accordance with the invention, mention may be made more particularly of the compounds corresponding to structures (II1) to (II12) below:

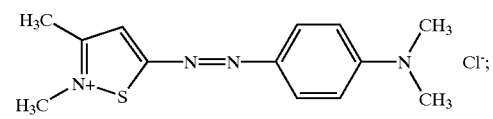
(II1)

(II2)

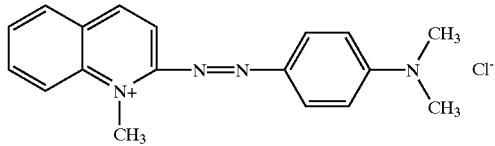
(II3)

(II4)

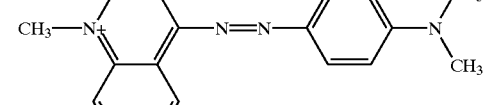
(II5)

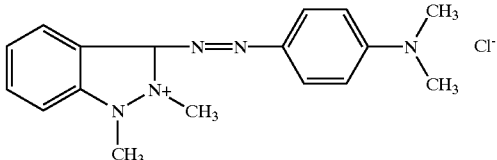
(II6)

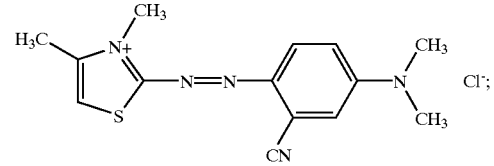
(II7)

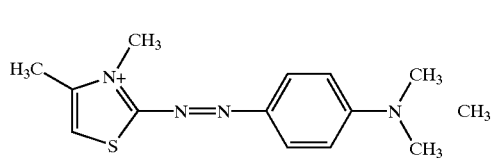
(II8)

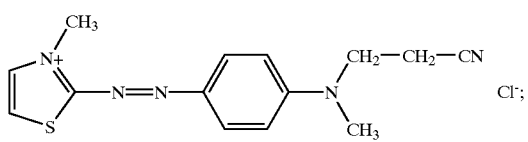
(II9)

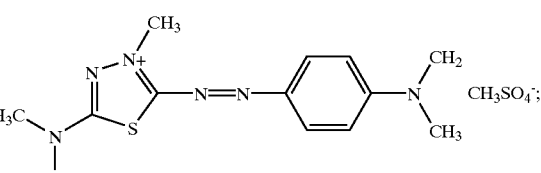
(II10)

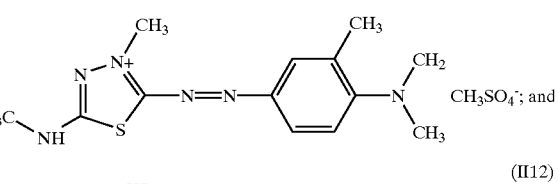
(II11)

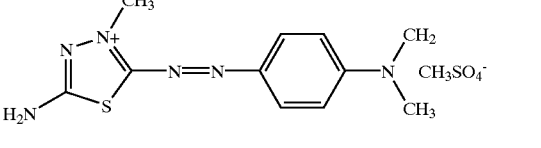
(II12)

Among the cationic direct dyes of formula (III) which can be used in the ready-to-use dye compositions in accordance with the invention, mention may be made more particularly of the compounds corresponding to structures (III1) to (III18) below:

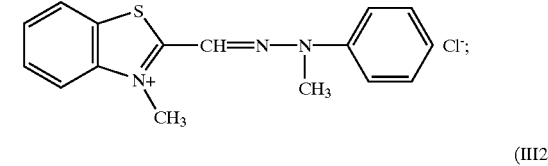
(III1)

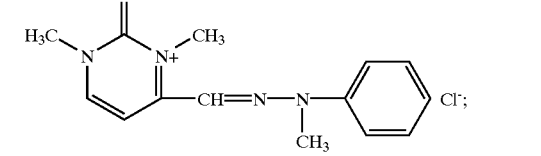
(III2)

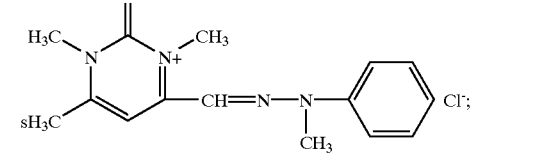
(III3)

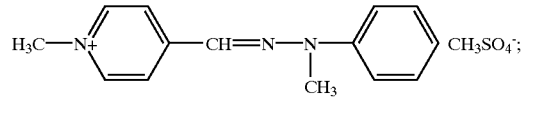
(III4)

-continued (III5) 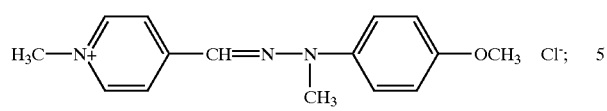

(III6) 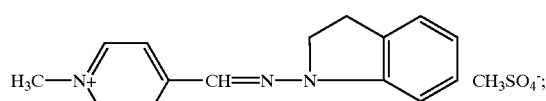

(III7) 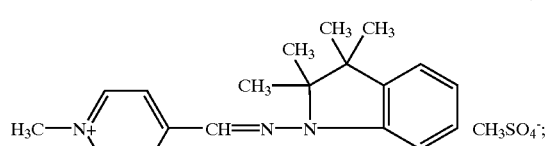

(III8) 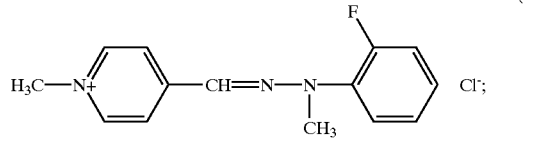

(III9) 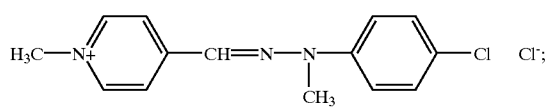

(III10) 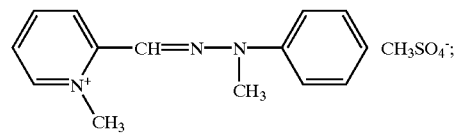

(II11) 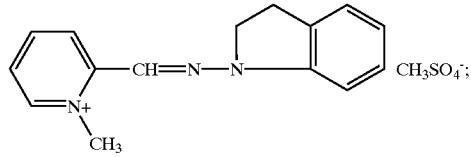

(II12) 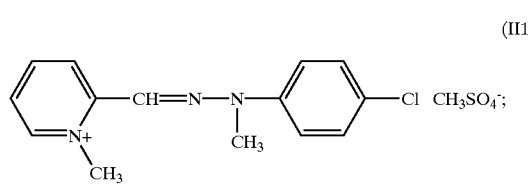

(II13) 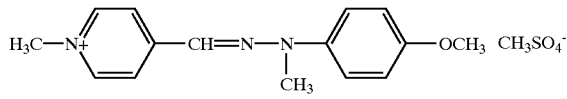

(II14) 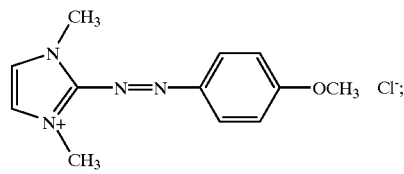

-continued (II15) 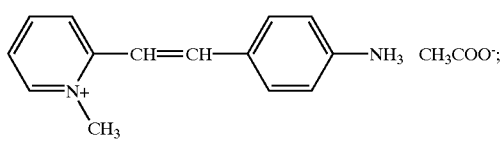

(II16) 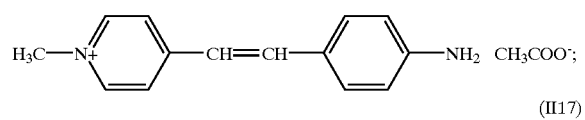

(II17) 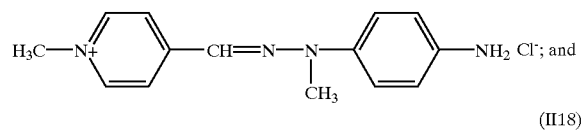

(II18) 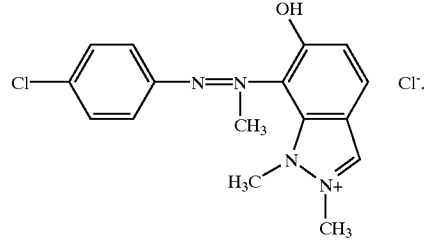

Among the specific compounds of structures (III1) to (III18) described above, the compounds most particularly preferred are the ones corresponding to structures (III4), (III5) and (III13).

Among the cationic direct dyes of formula (III') which can be used in the ready-to-use dye compositions in accordance with the invention, mention may be made more particularly of the compounds corresponding to structures (III'1) to (III'3) below:

(III'1) 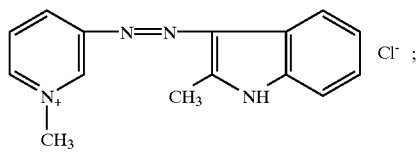

(III'2) 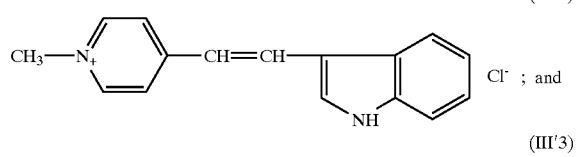

(III'3) 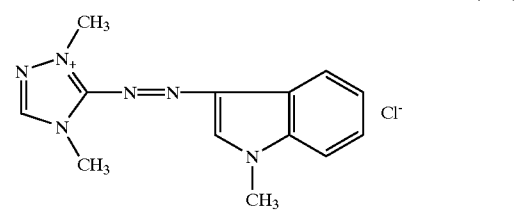

The cationic direct dye(s) used according to the invention preferably represent(s) from 0.001 to 10% by weight approximately relative to the total weight of the ready-to-use dye composition, and even more preferably from 0.05 to 5% by weight approximately relative to this weight.

The nature of the auto-oxidizable dye(s) used in the ready-to-use dye composition is not critical. It (they) can be chosen in particular from benzene, indole or indoline auto-oxidizable dyes.

Among the benzene auto-oxidizable dyes which can be used in the dye composition in accordance with the invention, mention may be made more particularly of the compounds of formula (IV) below, and the addition salts thereof with an acid:

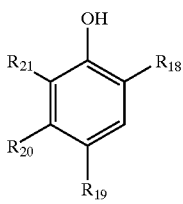

(IV)

in which:
- $R_{18}$ represents a hydrogen atom, a $C_1$–$C_4$ alkyl radical or an amino radical,
- $R_{19}$ represents a $C_1$–$C_4$ alkyl, hydroxyl, amino, mono($C_1$–$C_4$)alkylamino or di($C_1$–$C_4$)alkylamino radical,
- $R_{20}$ represents a hydrogen atom or a hydroxyl or amino radical,
- $R_{21}$ represents a hydrogen atom or an amino radical;

it being understood that at least two of the radicals $R_{19}$ to $R_{21}$ represent, independently of each other, a hydroxyl, amino, mono($C_1$–$C_4$)alkylamino or di($C_1$–$C_4$)alkylamino radical.

Among the benzene auto-oxidizable dyes of formula (IV) above, mention may be made more particularly of 1,2,4-trihydroxybenzene, 1-methyl-2,4,5-trihydroxybenzene, 2,4-diamino-6-methylphenol, 2-amino-4-methylaminophenol, 2,5-diamino-4-methyl-phenol, 2,6-diamino-4-diethylaminophenol and 2,6-diamino-1,4-dihydroxybenzene, and the addition salts thereof with an acid.

Among the indole and indoline auto-oxidizable dyes which can be used in the dye composition in accordance with the invention, mention may be made in particular of the compounds of formulae (V) and (VI) below:

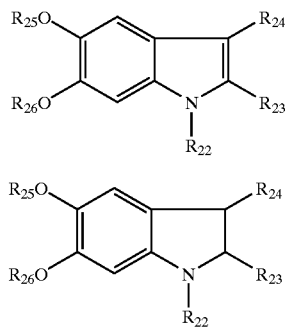

in which:
- $R_{22}$, $R_{24}$, $R_{25}$, and $R_{26}$, which may be identical or different, represent a hydrogen atom or a $C_1$–$C_4$ alkyl or $C_1$–$C_4$ acyl radical,
- $R_{23}$ represents a hydrogen atom, a $C_1$–$C_4$ alkyl radical or a carboxyl radical.

Among the auto-oxidizable dyes of formula (V) above, mention may be made more particularly of 5,6-dihydroxyindole, 2-methyl-5,6-dihydroxyindole, 3-methyl-5,6-dihydroxyindole, 1-methyl-5,6-dihydroxy-indole, 2,3-dimethyl-5,6-dihydroxyindole, 5-methoxy-6-hydroxyindole, 5-acetoxy-6-hydroxyindole, 5,6-diacetoxyindole and 5,6-dihydroxy-2-indole-carboxylic acid, and the addition salts thereof with an acid.

Among the auto-oxidizable dyes of formula (VI) above, mention may be made more particularly of 5,6-dihydroxyindoline, 1-methyl-5,6-dihydroxyindoline and 1-ethyl-5,6-dihydroxy-indoline, and the addition salts thereof with an acid.

The auto-oxidizable dye(s) preferably represent(s) from 0.0005 to 12% by weight approximately relative to the total weight of the dye composition in accordance with the invention, and even more preferably from 0.005 to 8% by weight approximately relative to this weight.

In order to facilitate the oxidation of the auto-oxidizable dyes, the ready-to-use dye composition in accordance with the invention can also contain one or more oxidizing agents. These oxidizing agents can be chosen in particular from hydrogen peroxide, urea peroxide, alkali metal bromates, persalts such as perborates and persulphates, and enzymes such as peroxidases and two-electron oxidoreductases.

Among the 2-electron oxidoreductases which can be used as oxidizing agents in the ready-to-use dye composition in accordance with the invention, mention may be made more particularly of pyranose oxidases, glucose oxidases, glycerol oxidases, lactate oxidases, pyruvate oxidases and uricases.

According to the invention, the use of uricases of animal, microbiological or biotechnological origin is particularly preferred.

By way of example, mention may be made in particular of the uricase extracted from boar liver, the uricase from *Arthrobacter globiformis* and the uricase from *Aspergillus flavus*.

The 2-electron oxidoreductase(s) can be used in pure crystalline form or in a form diluted in a diluent which is inert with respect to the said 2-electron oxidoreductase.

When they are used, the 2-electron oxidoreductase(s) in accordance with the invention preferably represent(s) from 0.01 to 200 by weight approximately relative to the total weight of the ready-to-use dye composition, and even more preferably from 0.1 to 50 by weight approximately relative to this weight.

When an enzyme of 2-electron oxidoreductase type is used in accordance with the invention, the ready-to-use dye composition can also contain one or more donors.

According to the invention, the term "donor" refers to the various substrates involved in the functioning of the said 2-electron oxidoreductase(s).

The nature of the donor (or substrate) used varies as a function of the nature of the 2-electron oxidoreductase which is used. For example, D-glucose, L-sorbose and D-xylose may be mentioned as donors for pyranose oxidases; D-glucose may be mentioned as a donor for glucose oxidases; glycerol and dihydroxyacetone may be mentioned as donors for glycerol oxidases; lactic acid and its salts may be mentioned as donors for lactate oxidases; pyruvic acid and its salts may be mentioned as donors for pyruvate oxidases; and lastly, uric acid and its salts may be mentioned as donors for uricases.

When they are used, the donor(s) (or substrate(s)) used in accordance with the invention preferably represent(s) from 0.01 to 20% by weight approximately relative to the total weight of the ready-to-use dye composition in accordance with the invention, and even more preferably from 0.1 to 5% approximately relative to this weight.

When the ready-to-use dye composition in accordance with the invention contains an oxidizing agent, it can also contain one or more oxidation bases and/or one or more couplers. These oxidation bases can be chosen in particular from para-phenylenediamines, para-aminophenols, ortho-phenylenediamines and heterocyclic bases such as, for example, pyridine derivatives, pyrimidine derivatives, pyrazole derivatives and pyrazolopyrimidine derivatives. The couplers can be chosen in particular from meta-phenylenediamines, meta-aminophenols, meta-diphenols, heterocyclic couplers such as, for example, indole derivatives, indoline derivatives, benzimidazole derivatives, benzomorpholine derivatives, sesamol derivatives, pyridine, pyrimidine and pyrazole derivatives, and the addition salts thereof with an acid.

When they are present, the oxidation base(s) preferably represent(s) from 0.0005 to 12% by weight approximately relative to the total weight of the dye composition in accordance with the invention, and even more preferably from 0.005 to 8% by weight approximately relative to this weight.

When they are present, the coupler(s) preferably represent(s) from 0.0001 to 10% by weight approximately relative to the total weight of the ready-to-use dye composition, and even more preferably from 0.005 to 80 by weight approximately relative to this weight.

In general, the addition salts with an acid which can be used in the context of the dye compositions of the invention (auto-oxidizable dyes, oxidation bases and couplers) are chosen in particular from the hydrochlorides, hydrobromides, sulphates, tartrates, lactates and acetates.

The medium which is suitable for dyeing (or support) for the ready-to-use dye composition in accordance with the invention generally consists of water or of a mixture of water and at least one organic solvent to dissolve the compounds which would not be sufficiently water-soluble. As organic solvents, mention may be made, for example, of $C_1$–$C_4$ alkanols, such as ethanol and isopropanol, as well as aromatic alcohols such as benzyl alcohol or phenoxyethanol, similar products and mixtures thereof.

The pH of the ready-to-use composition in accordance with the invention is generally between 5 and 11 approximately and preferably between 6.5 and 10 approximately. It can be adjusted to the desired value by means of acidifying or basifying aids usually used for dyeing keratin fibres.

Among the acidifying agents, mention may be made, by way of example, of inorganic or organic acids such as hydrochloric acid, orthophosphoric acid, sulphuric acid, carboxylic acids such as acetic acid, tartaric acid, citric acid and lactic acid, and sulphonic acids.

Among the basifying agents, mention may be made, by way of example, of aqueous ammonia, alkaline carbonates, alkanolamines such as mono-, di- and triethanolamine, 2-methyl-2-amino-1-propanol and derivatives thereof, sodium hydroxide, potassium hydroxide and the compounds of formula (VII) below:

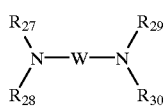

(VII)

in which W is a propylene residue optionally substituted with a hydroxyl group or a $C_1$–$C_4$ alkyl radical; $R_{27}$, $R_{28}$, $R_{29}$ and $R_{30}$, which may be identical or different, represent a hydrogen atom or a $C_1$–$C_4$ alkyl or $C_1$–$C_4$ hydroxyalkyl radical.

The ready-to-use dye composition in accordance with the invention can also contain various adjuvants conventionally used in compositions for dyeing the hair, such as, for example, antioxidants, penetrating agents, sequestering agents, fragrances, buffers, dispersing agents, preserving agents and opacifiers.

Needless to say, a person skilled in the art will take care to select this or these optional complementary compounds such that the advantageous properties intrinsically associated with the ready-to-use dye composition in accordance with the invention are not, or are not substantially, adversely affected by the addition(s) envisaged.

The ready-to-use dye composition in accordance with the invention can be in various forms, such as in the form of liquids, creams or gels, which may be pressurized, or in any other form which is suitable for dyeing keratin fibres, and in particular human hair. It must be free of gaseous oxygen, so as to avoid any premature oxidation of the auto-oxidizable dye(s).

A subject of the invention is also a process for dyeing keratin fibres, and in particular human keratin fibres such as the hair, using the ready-to-use dye composition as defined above.

According to this process, at least one ready-to-use dye composition as defined above is applied to the fibres, for a period which is sufficient to develop the desired coloration, after which the fibres are rinsed, optionally washed with shampoo, rinsed again and dried.

The time required to develop the coloration on the keratin fibres is generally between 3 and 60 minutes and even more precisely between 5 and 40 minutes.

According to one specific embodiment of the invention and when the ready-to-use composition in accordance with the invention contains an oxidizing agent, the process includes a preliminary step which consists in separately storing, on the one hand, a composition (A) comprising, in a medium which is suitable for dyeing, at least one cationic direct dye, and at least one auto-oxidizable dye, and, on the other hand, a composition (B) containing, in a medium which is suitable for dyeing, at least one oxidizing agent, and then in mixing them together at the time of use, before applying this mixture to the keratin fibres.

Another subject of the invention is a multi-compartment dyeing device or "kit" or any other multi-compartment packaging system, a first compartment of which contains composition (A) as defined above and a second compartment of which contains composition (B) as defined above. These devices can be equipped with a means for applying the desired mixture to the hair, such as the devices described in patent FR-2,586,913 in the name of the Applicant.

The examples which follow are intended to illustrate the invention without, however, limiting its scope.

EXAMPLES

Dyeing Examples 1 to 3

The following ready-to-use dye compositions were prepared (contents in grams):

| COMPOSITION | 1 | 2 | 3 |
|---|---|---|---|
| 5,6-Dihydroxyindoline monohydrobromide (auto-oxidizable dye) | 0.7 | — | — |
| 5,6-Dihydroxyindole (auto-oxidizable dye) | — | 0.5 | — |
| 1,2,4-Trihydroxybenzene (auto-oxidizable dye) | — | — | 1.2 |

-continued

| COMPOSITION | 1 | 2 | 3 |
|---|---|---|---|
| Cationic direct dye Basic Red 76 (Arianor Madder Red) | 0.1 | — | — |
| Orange-coloured cationic direct dye of structure (I4) | — | 0.07 | — |
| Red cationic direct dye of structure (I1) | — | — | 0.05 |
| Common dye support (*) | (*) | (*) | (*) |
| Demineralized water q.s. | 100 g | 100 g | 100 g |

(*): Common dye support:
| | |
|---|---|
| Ethanol | 20.0 g |
| Nonylphenol oxyethylenated with 9 mol of ethylene oxide, sold under the name Igepal NR 9 OR by the company Rhodia Chemie | 8.0 g |
| 2-Amino-2-methyl-1-propanol q.s. | pH = 8.0 |

Each of the ready-to-use dye compositions described above was applied to locks of natural grey hair containing 90% white hairs for 30 minutes. The hair was then rinsed, washed with a standard shampoo and then dried.

The hair was dyed in the shades featured in the table below:

| EXAMPLE | Shade obtained |
|---|---|
| 1 | Red-blonde |
| 2 | Coppery blonde |
| 3 | Mahogany blonde |

What is claimed is:

1. A ready-to-use composition for dyeing keratin fibers, comprising:
   at least one cationic direct dye and
   at least one auto-oxidizable dye chosen from benzene, indole, and indoline auto-oxidizable dyes,
      wherein when said at least one auto-oxidizable dye is chosen from benzene auto-oxidizable dyes, said benzene auto-oxidizable dyes are chosen from compounds of formula (IV) below and acid-addition salts thereof:

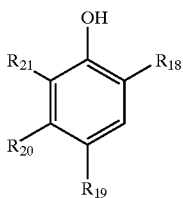

(IV)

in which:
   $R_{18}$ is chosen from a hydrogen atom, $C_1$–$C_4$ alkyl radicals, and amino radicals,
   $R_{19}$ is chosen from $C_1$–$C_4$ alkyl radicals, a hydroxyl radical, amino radicals, mono($C_1$–$C_4$)alkylamino radicals, and di($C_1$–$C_4$)alkylamino radicals,
   $R_{20}$ is chosen from a hydrogen atom, a hydroxyl radical, and amino radicals, and
   $R_{21}$ is chosen from a hydrogen atom and amino radicals;
   wherein at least two of the radicals $R_{19}$ to $R_{21}$ are chosen from, independently of each other, a hydroxyl radical, amino radicals, mono($C_1$–$C_4$) alkylamino radicals and di($C_1$–$C_4$)alkylamino radicals.

2. A ready-to-use composition according to claim 1, wherein said at least one cationic direct dye is chosen from cationic aminoanthraquinone dyes, cationic monoazo dyes, cationic diazo dyes, and cationic naphthoquinone dyes.

3. A ready-to-use composition according to claim 2, wherein said at least one cationic direct dye is chosen from (8-((p-aminophenyl)azo)-7-hydroxy-2-naphthyl) trimethylammonium chloride, 3-((4-amino-6-bromo-5,8-dihydro-1-hydroxy-8-imino-5-oxo-2-naphthalenyl)amino)-N,N,N-trimethylbenzenammonium chloride, 7-hydroxy-8-((2-methoxyphenyl)azo)-N,N,N-trimethyl-2-naphthalenammonium chloride, (8-((4-amino-2-nitrophenyl)azo)-7-hydroxy-2-naphthyl) trimethylammonium chloride and 3-((4,5-dihydro-3-methyl-5-oxo-1-phenyl-1H-pyrazol-4-yl)azo)-N,N,N-trimethylbenzenammonium chloride.

4. A ready-to-use composition according to claim 1, wherein said at least one cationic direct dye is chosen from:
   a) compounds of formula (I) below:

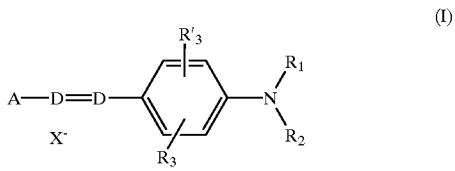

(I)

in which:
   D is chosen from a nitrogen atom and a —CH group,
   $R_1$ and $R_2$, which may be identical or different, are chosen from a hydrogen atom; a 4'-aminophenyl radical; and $C_1$–$C_4$ alkyl radicals which can be substituted with a —CN, —OH or —NH$_2$ radical; or form, with a carbon atom of the benzene ring, an optionally oxygenated or nitrogenous heterocycle, which can be substituted with one or more $C_1$–$C_4$ alkyl radicals;
   $R_3$ and $R'_3$, which may be identical or different, are chosen from a hydrogen atom, halogen atoms chosen from chlorine, bromine, iodine and fluorine, cyano radicals, $C_1$–$C_4$ alkoxy radicals, and acetyloxy radicals,
   $X^-$ is chosen from anions,
   A is chosen from compounds A1 to A19 below:

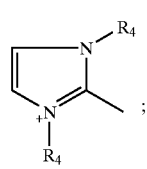

A1

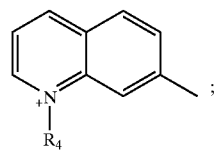

A2

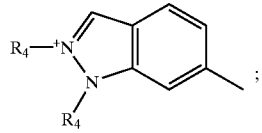

A3

-continued

A₄ 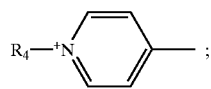

A₅ 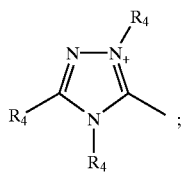

A₆ 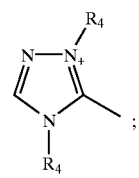

A₇ 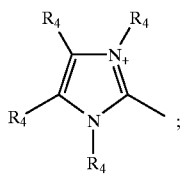

A₈ 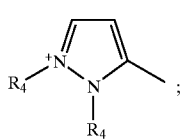

A₉ 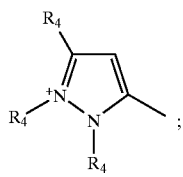

A₁₀ 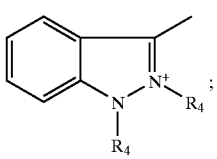

A₁₁ 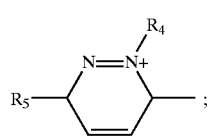

A₁₂ 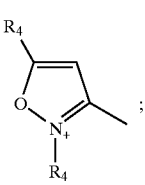

A₁₃ 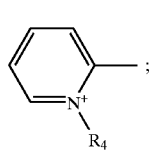

-continued

A₁₄ 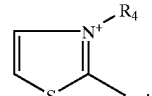

A₁₅ 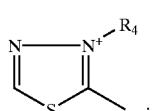

A₁₆ 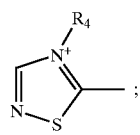

A₁₇ 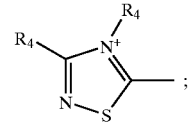

A₁₈ 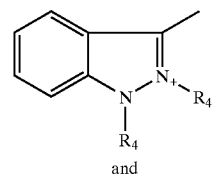

and

A₁₉ 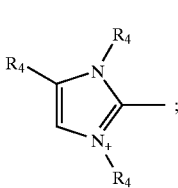

in which:
$R_4$ is chosen from $C_1$–$C_4$ alkyl radicals which can be substituted with a hydroxyl radical; and,
$R_5$ is chosen from $C_1$–$C_4$ alkoxy radicals,
wherein when D is —CH, when A is $A_4$ or $A_{13}$ and when $R_3$ is other than an alkoxy radical, then $R_1$ and $R_2$ are not simultaneously a hydrogen atom;

b) compounds of formula (II) below:

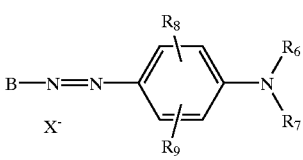

(II)

in which:
$R_6$ is chosen from a hydrogen atom and $C_1$–$C_4$ alkyl radicals,
$R_7$ is chosen from a hydrogen atom, a 4'-aminophenyl radical, and alkyl radicals which can be substituted with a —CN radical or with an amino group, or forms, with $R_6$, a heterocycle which can be an oxygenated heterocycle, a nitrogeneous heterocycle, or both, and which can be substituted with $C_1$–$C_4$ alkyl radicals, $R_8$ and $R_9$, which may be identical or different, are chosen from a hydrogen atom, halogen atoms, $C_1$–$C_4$ alkyl radicals, $C_1$–$C_4$ alkoxy radicals, and a —CN radical, $X^-$ is chosen from anions, B is chosen from compounds B1 to B6 below:

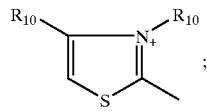
B1

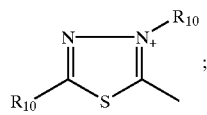
B2

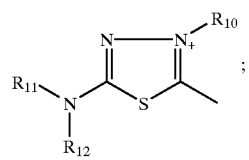
B3

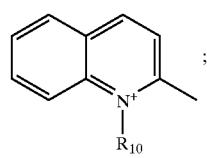
B4

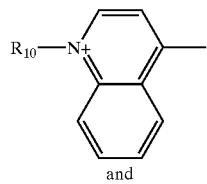
B5 and

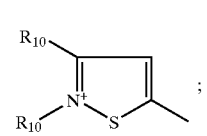
B6 in which $R_{10}$ is chosen from $C_1$–$C_4$ alkyl radicals, $R_{11}$ and $R_{12}$, which may be identical or different, are chosen from a hydrogen atom, and $C_1$–$C_4$ alkyl radicals;

c) compounds of formulae (III) and (III') below:

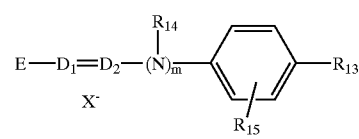
(III)

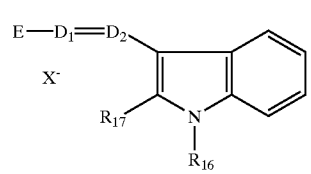
(III')

in which:

$R_{13}$ is chosen from a hydrogen atom, $C_1$–$C_4$ alkoxy radicals, halogen atoms, and amino radicals, $R_{14}$ is chosen from a hydrogen atom, and $C_1$–$C_4$ alkyl radicals, or forms, with a carbon atom of the benzene ring, a heterocycle which is optionally oxygenated and which can be substituted with one or more $C_1$–$C_4$ alkyl groups, $R_{15}$ is chosen from a hydrogen atom, and halogen atoms, $R_{16}$ and $R_{17}$, which may be identical or different, are chosen from a hydrogen atom, and $C_1$–$C_4$ alkyl radicals, $D_1$ and $D_2$, which may be identical or different, are chosen from a nitrogen atom, and a —CH group, m is 0 or 1, wherein when $R_{13}$ is an unsubstituted amino group, then $D_1$ and $D_2$ are both a —CH group and m is 0, $X^-$ is chosen from anions, E is chosen from compounds E1 to E8 below:

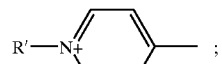
E1

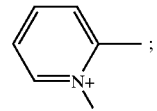
E2

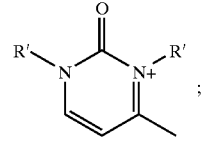
E3

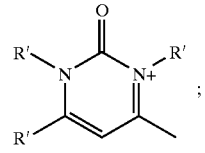
E4

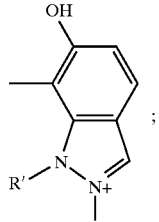
E5

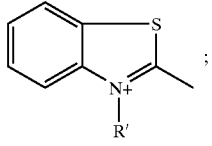
E6

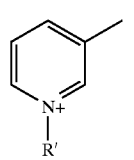
E7 and

-continued

E8
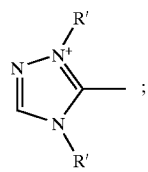

in which:

R' is chosen from $C_1$–$C_4$ alkyl radicals; wherein when m is 0 and when $D_1$ is a nitrogen atom, then E can also be chosen from compound E9 below:

E9
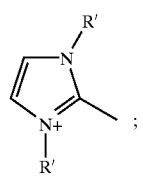

in which R' is chosen from $C_1$–$C_4$ alkyl radicals.

5. A ready-to-use composition according to claim 4, wherein said anions are chosen from chloride, methyl sulfate, and acetate.

6. A ready-to-use composition according to claim 4, wherein when $R_8$, $R_9$, $R_{13}$, or $R_{15}$ are halogens, said halogens are chosen from bromine, chlorine, iodine and fluorine.

7. A ready-to-use composition according to claim 1, wherein said at least one cationic direct dye of formula (I) is chosen from compounds (I1) to (I52) below:

(I1)
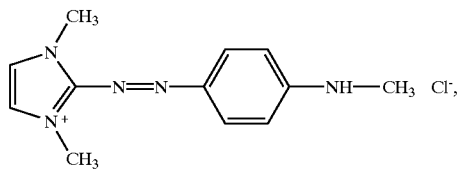

(I2)
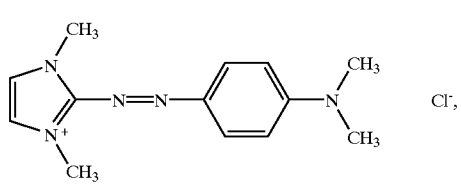

(I3)
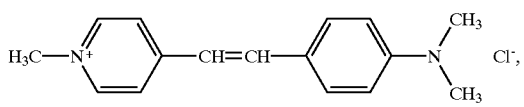

(I4)
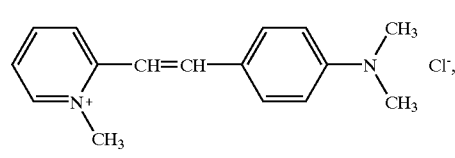

(I-5)
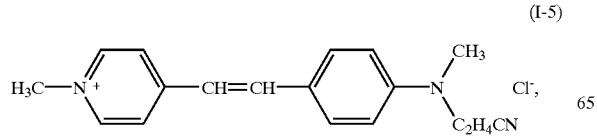

(I-6)
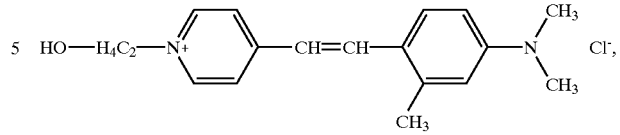

(I7)
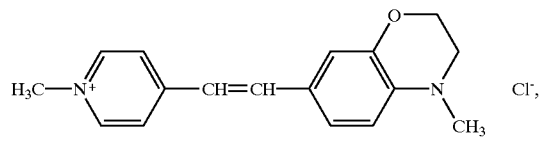

(I8)
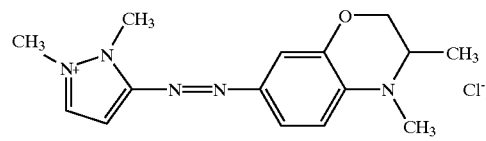

(I9)
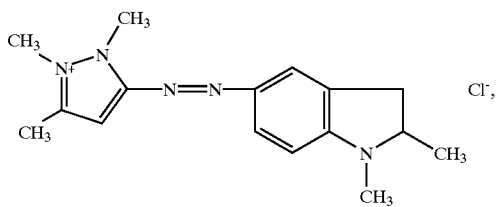

(I10)
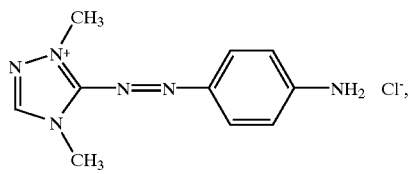

(I11)
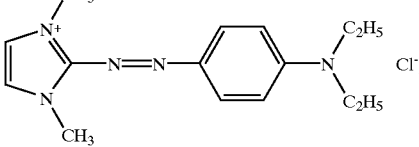

(I12)
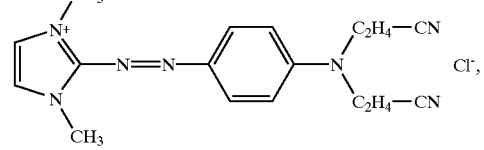

(I13)
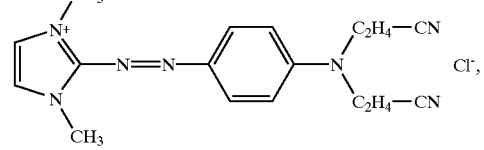

(I14)
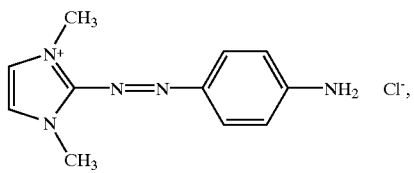

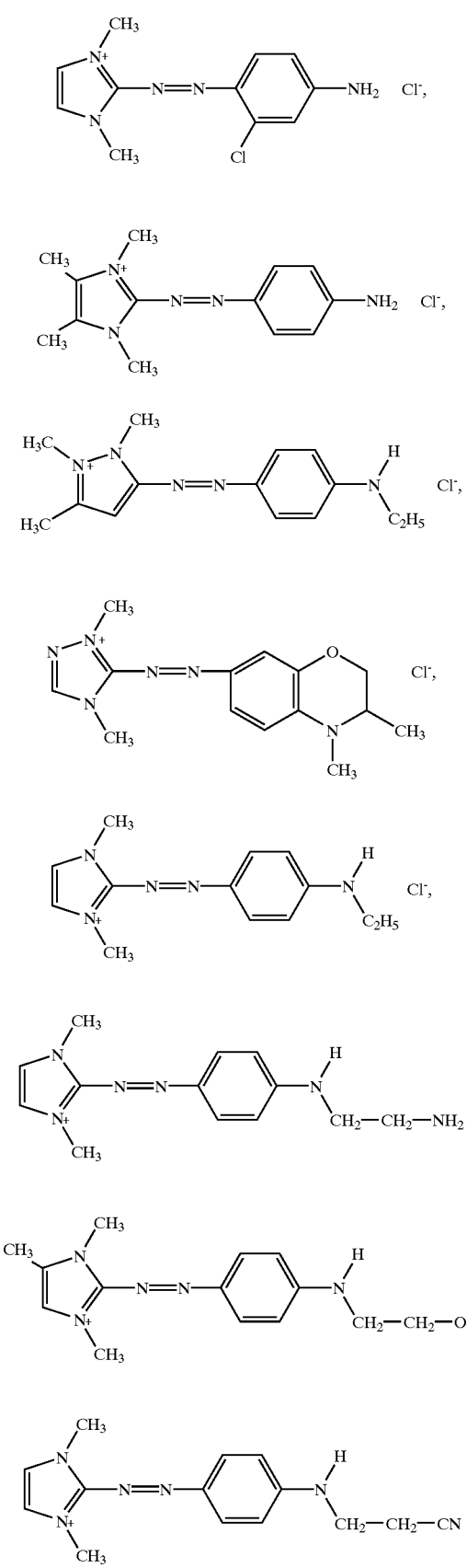
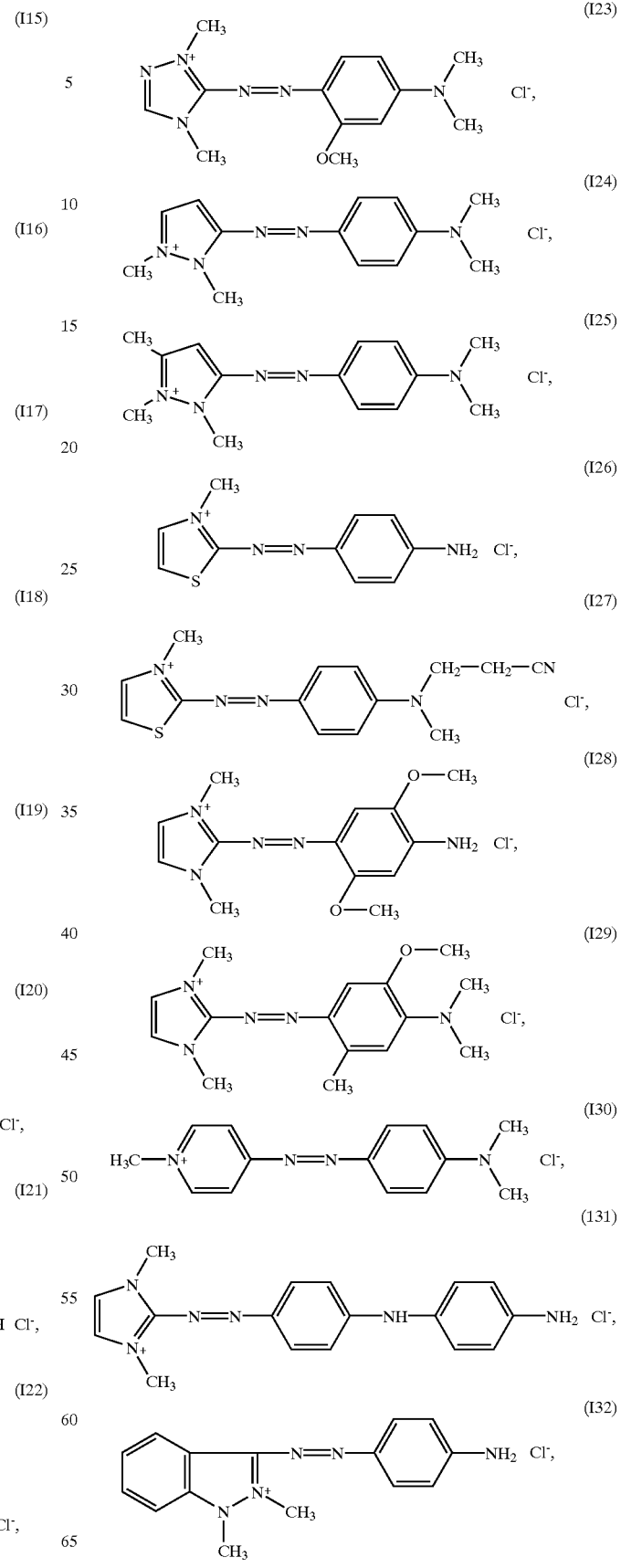

-continued
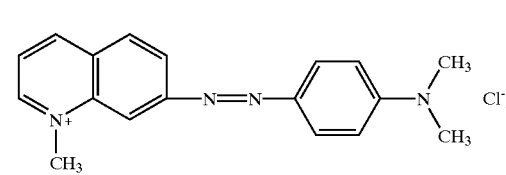 (I33)
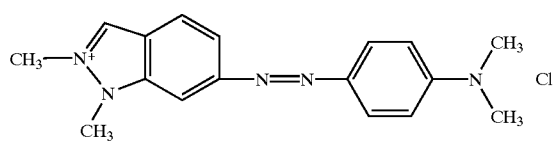 (I34)
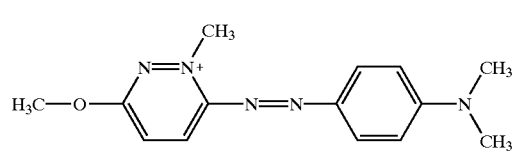 (I35)
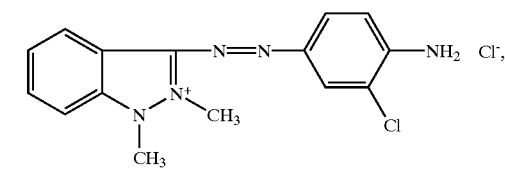 (I36)
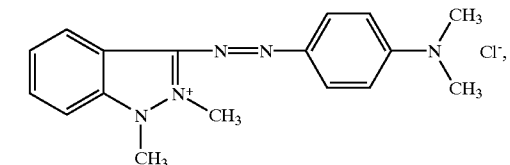 (I37)
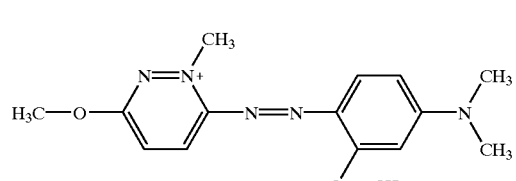 (I38)
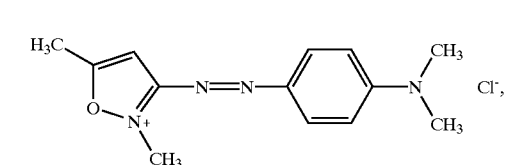 (I39)
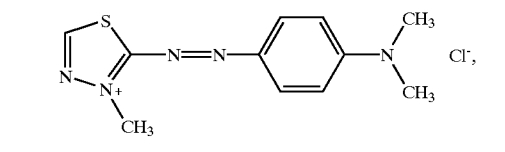 (I40)
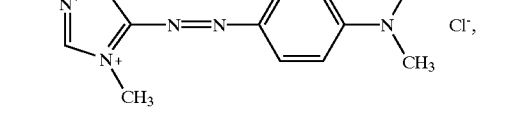 (I41)
-continued
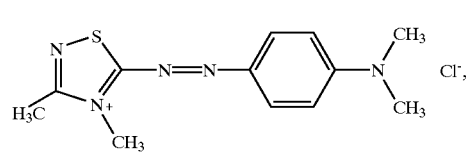 (I42)
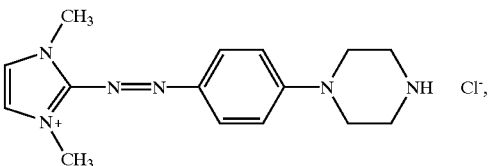 (I43)
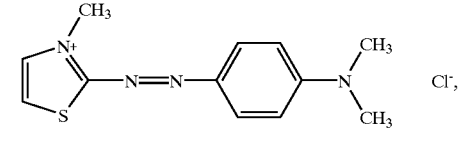 (I44)
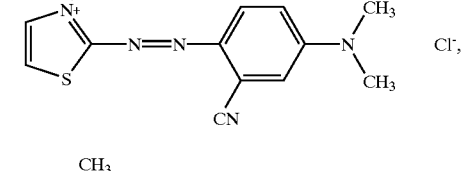 (I45)
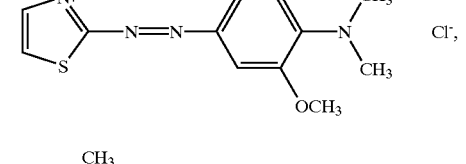 (I46)
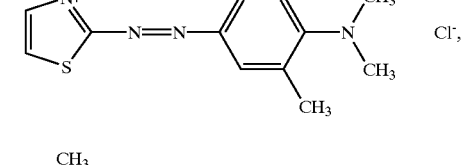 (I47)
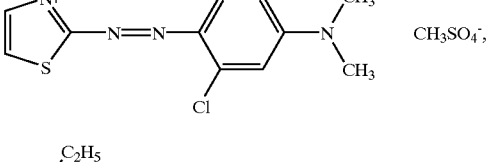 (I48)
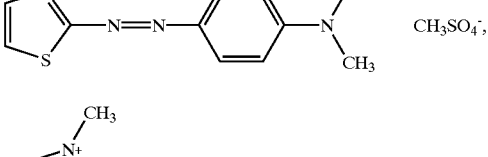 (I49)
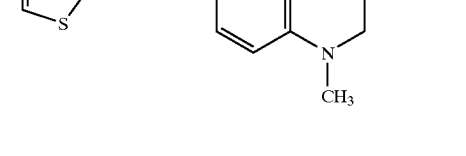 (I50)

-continued
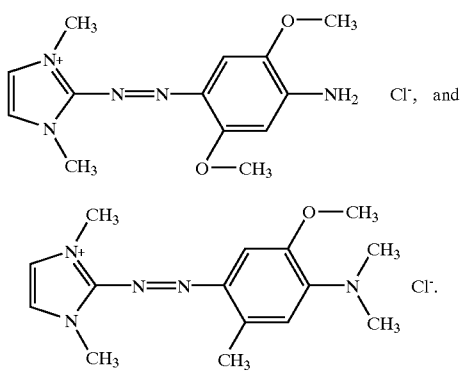 (I51)
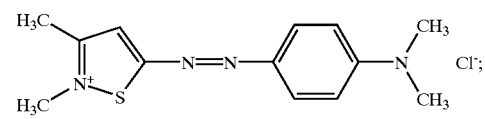 (I52)
8. A ready-to-use composition according to claim 1, wherein said at least one cationic direct dye of formula (II) is chosen from compounds (II1) to (II12) below:
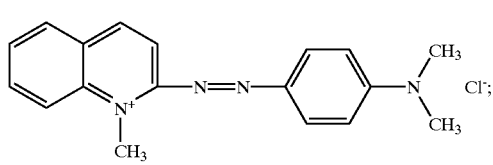 (II1)
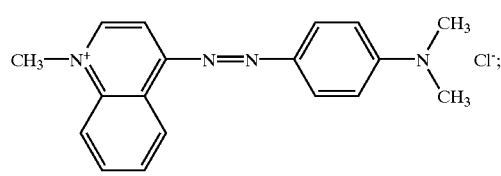 (II2)
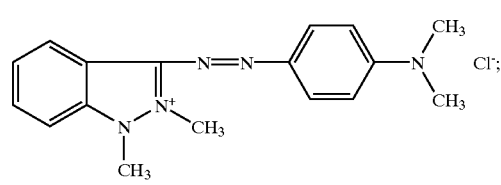 (II3)
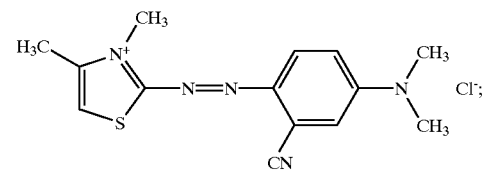 (II4)
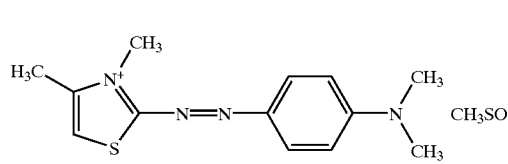 (II5)
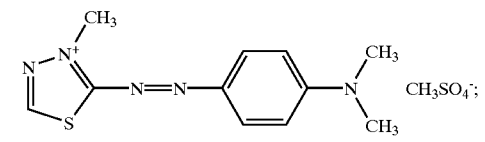 (II6)
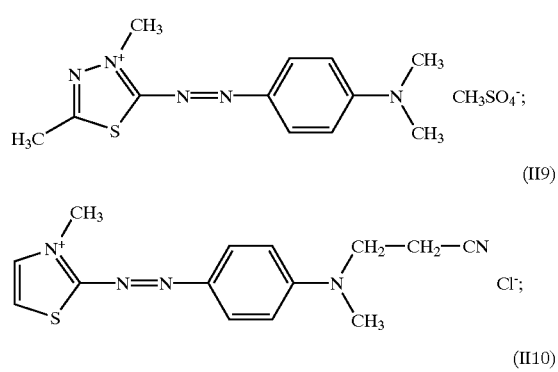 (II7)
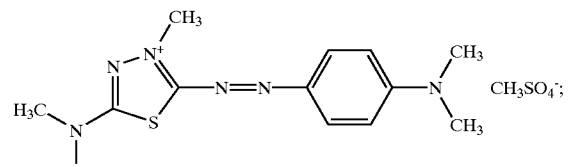 (II8)
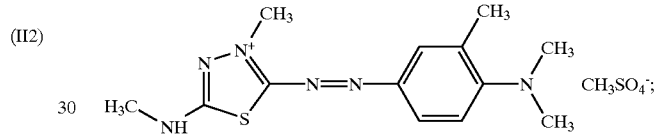 (II9)
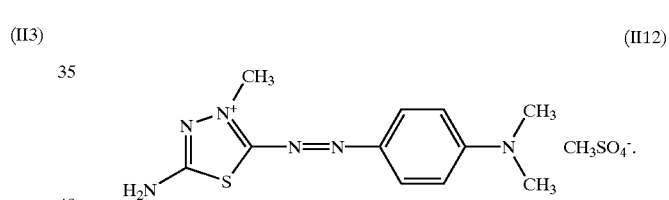 (II10)
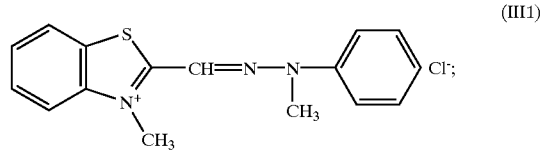 (II11)
and
 (II12)
9. A ready-to-use composition according to claim 1, wherein said at least one cationic direct dye is chosen from compounds (III1) to (III18) below:
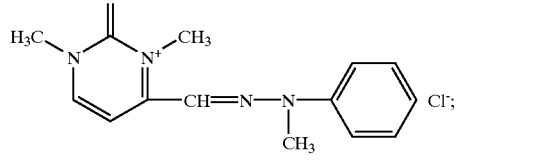 (III1)
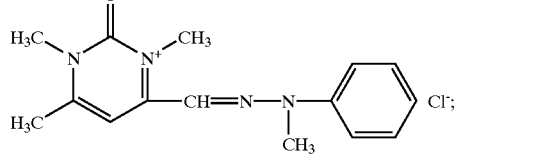 (III2)
(III3)

-continued
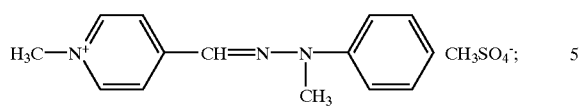 (III4)
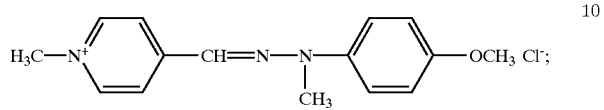 (III5)
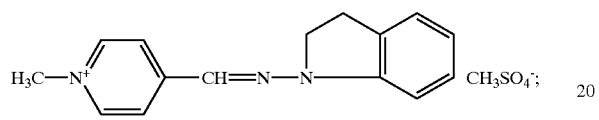 (III6)
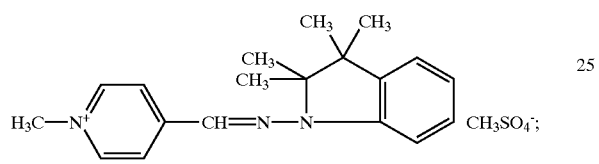 (III7)
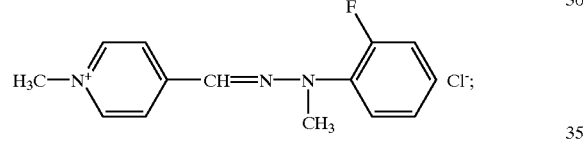 (III8)
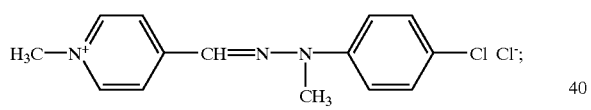 (III9)
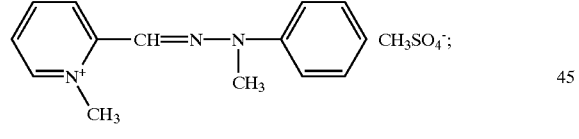 (III10)
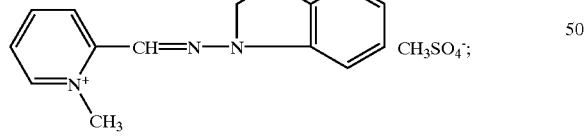 (III11)
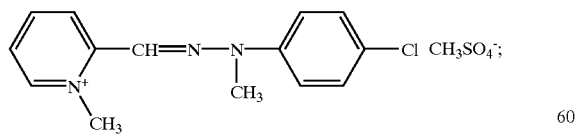 (III12)
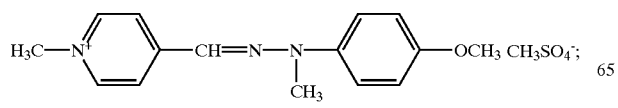 (III13)
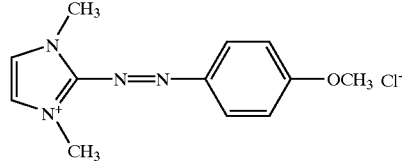 (III14)
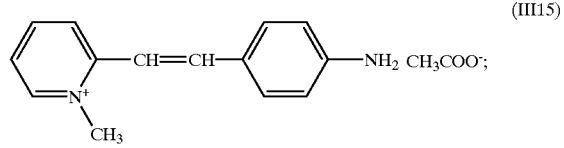 (III15)
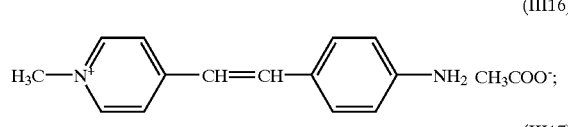 (III16)
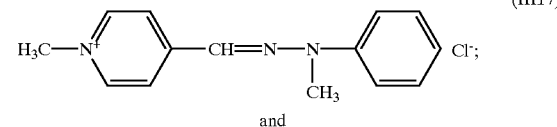 (III17)
and
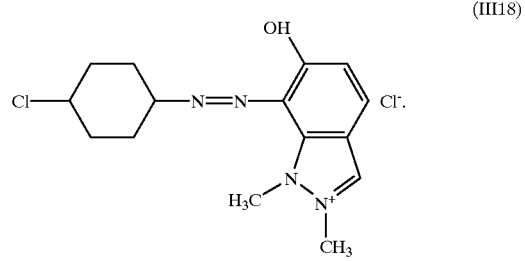 (III18)
10. A ready-to-use composition according to claim 1, wherein said at least one cationic direct dye is chosen from compounds (III'1) to (III'3) below:
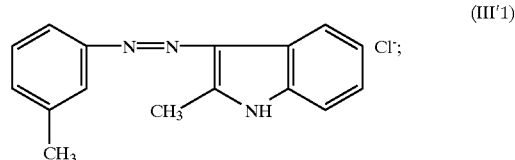 (III'1)
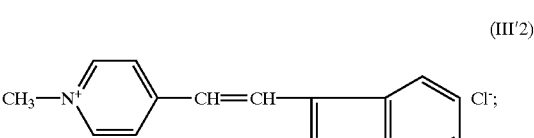 (III'2)
and
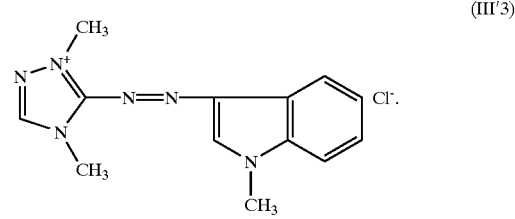 (III'3)

11. A ready-to-use composition according to claim 1, wherein said at least one cationic direct dye is present in said composition in an amount ranging from 0.001 to 10% by weight relative to the total weight of the ready-to-use dye composition.

12. A ready-to-use composition according to claim 11, wherein said at least one cationic direct dye is present in an amount ranging from 0.05 to 5% by weight relative to the total weight of said composition.

13. A ready-to-use composition according to claim 1, wherein said at least one benzene auto-oxidizable dye of formula (IV) is chosen from 1,2,4-trihydroxybenzene, 1-methyl-2,4,5trihydroxybenzene, 2,4-diamino-6-methylphenol, 2-amino-4-methylaminophenol, 2,5diamino-4-methylphenol, 2,6-diamino-4-diethylaminophenol and 2,6-diamino-1,4dihydroxybenzene, and the acid-addition salts thereof.

14. A ready-to-use composition according to claim 13, wherein said acid-addition salts are chosen from hydrochlorides, hydrobromides, sulphates, tartrates, lactates and acetates.

15. A ready-to-use composition according to claim 1, wherein said at least one indole and said at least one indoline auto-oxidizable dyes are chosen from compounds of formulae (V) and (VI) below and the acid-addition salts thereof:

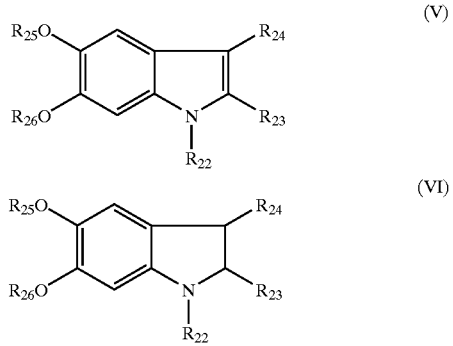

in which:
- $R_{22}$, $R_{24}$, $R_{25}$ and $R_{26}$, which may be identical or different, are chosen from a hydrogen atom, $C_1$–$C_4$ alkyl and $C_1$–$C_4$ acyl radicals, and
- $R_{23}$ is chosen from a hydrogen atom, $C_1$–$C_4$ alkyl radicals, and carboxyl radicals.

16. A ready-to-use composition according to claim 15, wherein said at least one auto-oxidizable dye of formula (V) is chosen from 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole, 5-methoxy-6-hydroxyindole, 5-acetoxy-6-hydroxyindole, 5,6-diacetoxyindole and 5,6-dihydroxy-2-indolecarboxylic acid, and the acid-addition salts thereof.

17. A ready-to-use composition according to claim 16, wherein the acid-addition salts are chosen from hydrochlorides, hydrobromides, sulphates, tartrates, lactates, and acetates.

18. A ready-to-use composition according to claim 15, wherein said at least one auto-oxidizable dye of formula (VI) is chosen from 5,6-dihydroxyindoline, 1-methyl-5,6-dihydroxyindoline and 1-ethyl-5,6-dihydroxyindoline, and the acid-addition salts thereof.

19. A ready-to-use composition according to claim 18, wherein the acid-addition salts are chosen from hydrochlorides, hydrobromides, sulphates, tartrates, lactates, and acetates.

20. A ready-to-use composition according to claim 1, wherein said at least one auto-oxidizable dye is present in said ready-to-use composition in an amount ranging from 0.0005 to 12% by weight relative to the total weight of said ready to use composition.

21. A ready-to-use composition according to claim 20, wherein said at least one auto-oxidizable dye is present in an amount ranging from 0.005 to 8% by weight relative to the total weight of said composition.

22. A ready-to-use composition according to claim 1, wherein said composition further comprises at least one oxidizing agent chosen from hydrogen peroxide, urea peroxide, alkali metal bromates, persalts, and enzymes.

23. A ready-to-use composition according to claim 22, wherein said persalts are chosen from perborates and persulphates.

24. A ready-to-use composition according to claim 22, wherein said enzymes are chosen from peroxidases and two-electron oxidoreductases.

25. A ready-to-use composition according to claim 24, wherein the two-electron oxidoreductases are chosen from pyranose oxidases, glucose oxidases, glycerol oxidases, lactate oxidases, pyruvate oxidases and uricases.

26. A ready-to-use composition according to claim 25, wherein the 2-electron oxidoreductases are chosen from uricases of animal, microbiological and biotechnological origin.

27. A ready-to-use composition according to claim 22, wherein said ready-to-use composition comprises at least one two-electron oxidoreductase and said at least one two-electron oxidoreductase is present in said composition in an amount ranging from 0.01 to 20% by weight relative to the total weight of said ready-to-use composition.

28. A ready-to-use composition according to claim 27, wherein said at least one 2-electron oxidoreductase is present in an amount ranging from 0.1 to 5% by weight relative to the total weight of said ready-to-use composition.

29. A ready-to-use composition according to claim 24, further comprising at least one donor for said at least one two-electron oxidoreductase, said donor being chosen from uric acid and its salts.

30. A ready-to-use composition according to claim 22, further comprising an additional ingredient chosen from:
- at least one oxidation base chosen from para-phenylenediamines, para-aminophenols, ortho-phenylenediamines and heterocyclic bases; and
- at least one coupler chosen from meta-phenylenediamines, meta-aminophenols, meta-diphenols, and heterocyclic couplers.

31. A ready-to-use composition according to claim 30, wherein said heterocyclic couplers are chosen from indole derivatives, indoline derivatives, benzimidazole derivatives, benzomorpholine derivatives, sesamol derivatives, pyridine, pyrimidine and pyrazole derivatives, and acid-addition salts thereof.

32. A ready-to-use composition according to claim 31, wherein the acid-addition salts are chosen from hydrochlorides, hydrobromides, sulphates, tartrates, lactates, and acetates.

33. A ready-to-use composition according to claim 30, wherein said at least one oxidation base is present in said composition in an amount ranging from 0.0005 to 12% by weight relative to the total weight of said composition.

34. A ready-to-use composition according to claim 30, wherein said at least one coupler is present in said composition in an amount ranging from 0.0001 to 10% by weight relative to the total weight of said composition.

35. A ready-to-use composition according to claim 30, wherein said at least one oxidation base is present in an amount ranging from 0.005 to 8% by weight relative to the total weight of said ready-to-use composition.

36. A ready-to-use composition according to claim 35, wherein said at least one coupler is present in an amount ranging from 0.005 to 8% by weight relative to the total weight of said composition.

37. A ready-to-use composition according to claim 1, further comprising water or a mixture of water and at least one organic solvent.

38. A ready-to-use composition according to claim 1, said composition having a pH ranging from 5 to 11.

39. A process for dyeing keratin fibers, comprising:
applying at least one ready-to-use dye composition to said fibers for a period of time sufficient to develop a desired coloration, wherein said ready-to-use composition comprises:
at least one cationic direct dye; and
at least one auto-oxidizable dye chosen from benzene, indole, and indoline auto-oxidizable dyes,
wherein when said at least one auto-oxidizable dv is chosen from benzene auto-oxidizable dyes, said benzene auto-oxidizable dyes are chosen from compounds of formula (IV) below and acid-addition salts thereof:

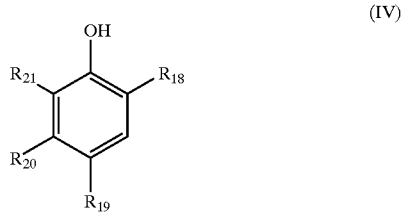

in which:
$R_{18}$ is chosen from a hydrogen atom, $C_1$–$C_4$ alkyl radicals, and amino radicals,
$R_{19}$ is chosen from $C_1$–$C_1$ alkyl radicals, a hydroxyl radical, amino radicals, mono($C_1$–$C_4$)alkylamino radicals, and di($C_1$–$C_4$)alkylamino radicals,
$R_{20}$ is chosen from a hydrogen atom, a hydroxyl radical and amino radicals, and
$R_{21}$ is chosen from a hydrogen atom and amino radicals;
wherein at least two of the radicals $R_{19}$ to $R_{21}$ are chosen from, independently of each other, a hydroxyl radical, amino radicals, mono($C_1$–$C_4$) alkylamino radicals and di($C_1$–$C_4$)alkylamino radicals.

40. A process according to claim 39, wherein:
said at least one cationic direct dye is chosen from cationic aminoanthraquinone dyes, cationic monoazo dyes, cationic diazo dyes, and cationic naphthoquinone dyes.

41. A process according to claim 40, wherein said at least one auto-oxidizable dye is chosen from 1,2,4-trihydroxybenzene, 1-methyl-2,4,5-trihydroxybenzene, 2,4-diamino-6-methylphenol, 2-amino-4-methylaminophenol, 2,5-diamino-4-methyl-phenol, 2,6-diamino-4-diethylaminophenol, 2,6-diamino-1,4-dihydroxybenzene, 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole, 5-methoxy-6-hydroxyindole, 5-acetoxy-6-hydroxyindole, 5,6-diacetoxyindole, 5,6-dihydroxy-2-indolecarboxylic acid, 5,6-dihydroxyindoline, 1-methyl-5,6-dihydroxyindoline, 1-ethyl-5,6-dihydroxyindoline, and the acid-addition salts thereof.

42. A process for dyeing keratin fibers, comprising:
storing a first composition separately from a second composition;
mixing said first and second compositions together; and,
applying the mixture to said fibers for a period of time sufficient to develop a desired color,
wherein said first composition comprises at least one cationic direct dye and at least one auto-oxidizable dye, and said second composition comprises at least one oxidizing agent.

43. A multi-compartment dyeing kit, comprising:
a first compartment and a second compartment, wherein said first compartment contains a first composition comprising at least one cationic direct dye and at least one auto-oxidizable dye, and said second compartment contains a composition comprising at least one oxidizing agent.

* * * * *

UNITED STATES PATENT AND TRADEMARK OFFICE
CERTIFICATE OF CORRECTION

PATENT NO.    : 6,503,283 B1
DATED         : January 7, 2003
INVENTOR(S)   : Gérard Lang et al.

It is certified that error appears in the above-identified patent and that said Letters Patent is hereby corrected as shown below:

<u>Title page,</u>
Item [75], Inventors, "Regaar" should read -- Saint Prix --.

<u>Column 27,</u>
Line 33, after "dye", delete "of formula (I)".
In the structure for compound (I5), "(I-5)" should read -- (I5) --.

<u>Column 28,</u>
In the structure for compound (I6), "(I-6)" should read -- (I6) --.

<u>Column 30,</u>
In the structure for compound (I31), "(131)" should read -- (I31) --.

<u>Column 32,</u>
In the structure for compound (I45), "(45)" should read -- (I45) --.
In the structure for compound (I47), "(47)" should read -- (I47) --.

<u>Column 33,</u>
Line 19, after "dye", delete "of formula (II)".

<u>Column 36,</u>
After the structure for compound (III14), insert a semicolon.
In the structure for compound (III18),

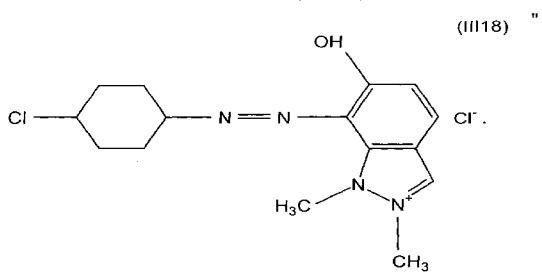

should read

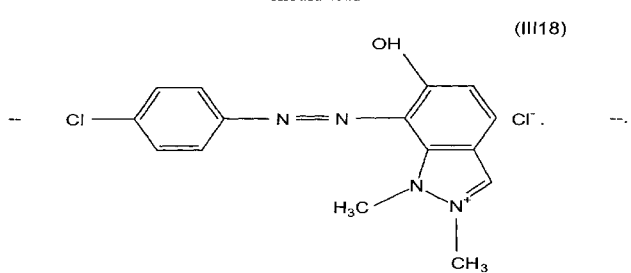

UNITED STATES PATENT AND TRADEMARK OFFICE
CERTIFICATE OF CORRECTION

PATENT NO.   : 6,503,283 B1  
DATED        : January 7, 2003  
INVENTOR(S)  : Gérard Lang et al.

Page 2 of 3

It is certified that error appears in the above-identified patent and that said Letters Patent is hereby corrected as shown below:

Column 36 cont'd,
In the structure for compound (III'1),

"  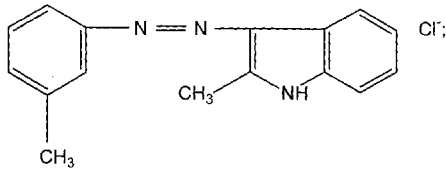  (III'1)  "

should read (III'1)  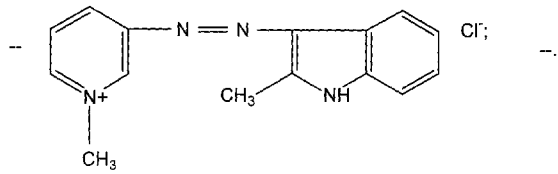

-- --.

Column 37,
Line 3, before "composition", insert -- ready-to-use --.
Line 9, after "said", insert -- ready-to-use --.
Line 12, "1-methyl-2,4,5trihydroxybenzene" should read
-- 1-methyl-2,4,5-trihydroxybenzene --.
Lines 13-14, "2,5diamino-4-methylphenol" should read
-- 2,5-diamino-4-methylphenol --.
Line 15, "2,6-diamino-1,4dihydroxybenzene" should read
-- 2,6-diamino-1,4-dihydroxybenzene --.

Column 38,
Line 5, "ready to use" should read -- ready-to-use --.
Line 9, after "said", insert -- ready-to-use --.
Line 28, "claim 22" should read -- claim 24 --.
Line 31, after "said", insert -- ready-to-use --.
Line 62, before "composition" insert -- ready-to-use --.
Lines 63, 65 and 67, after "said", insert -- ready-to-use --.

UNITED STATES PATENT AND TRADEMARK OFFICE
CERTIFICATE OF CORRECTION

PATENT NO. : 6,503,283 B1
DATED : January 7, 2003
INVENTOR(S) : Gérard Lang et al.

It is certified that error appears in the above-identified patent and that said Letters Patent is hereby corrected as shown below:

<u>Column 39,</u>
Line 8, after "said", insert -- ready-to-use --.
Line 21, "dv" should read -- dye --.
Line 39, "$C_1$-$C_1$" should read -- $C_1$-$C_4$ --.
Line 43, after "radical", insert a comma.

Signed and Sealed this

Fifteenth Day of July, 2003

JAMES E. ROGAN
*Director of the United States Patent and Trademark Office*